United States Patent [19]
Stringer et al.

[11] Patent Number: 4,663,482
[45] Date of Patent: May 5, 1987

[54] INTERMEDIATES FOR PREPARING 7-(2-AMINOETHYL)-1,3-BENZTHIA- OR OXA- ZOL-2(3H)-ONES

[75] Inventors: Orum D. Stringer, Philadelphia; Joseph Weinstock, Phoenixville, both of Pa.

[73] Assignee: SmithKline Beckman Corporation, Philadelphia, Pa.

[21] Appl. No.: 787,896

[22] Filed: Oct. 16, 1985

Related U.S. Application Data

[62] Division of Ser. No. 649,466, Sep. 12, 1984, Pat. No. 4,554,284.

[51] Int. Cl.$^4$ .................... C07C 91/44; C07C 149/42
[52] U.S. Cl. .................................................. 564/374
[58] Field of Search ........................................ 564/374

[56] References Cited

U.S. PATENT DOCUMENTS 3,227,758  1/1966  Richter ............................... 564/374

OTHER PUBLICATIONS

Tranzer et al., Experientia, 29, 314 (1973).

Primary Examiner—Robert Gerstl
Attorney, Agent, or Firm—Joseph A. Marlino; Stuart R. Suter; Alan D. Lourie

[57] ABSTRACT

Certain 2-amino-6-ω-aminoethylphenols and thiophenols are intermediates for preparing $D_2$-dopamine agonistic aminoethyl substituted 1,3-benzthiazol- and 1,3-benzoxazol-2(3H)-ones.

4 Claims, No Drawings

INTERMEDIATES FOR PREPARING 7-(2-AMINOETHYL)-1,3-BENZTHIA- OR OXAZOL-2(3H)-ONES

This is a division of application Ser. No. 649,446 filed Sept. 12, 1984, now U.S. Pat. No. 4,554,284.

This invention relates to chemical intermediates for preparing 1,3-benzthiazol-2(3H)-ones or 1,3-benzoxazol-(2(3H)-ones which have an aminoethyl substituent in the benz ring. The compounds have potent $D_2$-agonist activity which is of use for treating hypertension.

DESCRIPTION OF THE PRIOR ART

U.S. Pat. No. 4,314,944 discloses the anti-hypertensive activity of certain aminoalkyl-2(3H)-indolones. U.S. Pat. No. 4,452,880 discloses related indolones. An earlier filed, and commonly assigned, patent application, U.S. Ser. No. 488,868 filed Apr. 26, 1983, discloses that certain carbostyril derivatives have dopaminergic activity.

The prior art does not teach the preparation of any $D_2$-agonist compounds which have an additional hetero member substituted in the nucleus of their structures. Such compounds have proved, in our hands, difficult to prepare and have been demonstrated to be very active $D_2$-agonists.

DESCRIPTION OF THE INVENTION

The compounds of this invention are illustrated by the following structural formula:

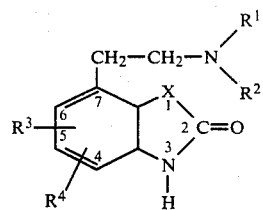

in which:

X is —S— or —O—;

$R^1$ and $R^2$ are, each, hydrogen, $C_{1-6}$-alkyl, allyl, benzyl, phenethyl, methoxyphenethyl or hydroxyphenethyl; and $R^3$ and $R^4$ are, each, hydrogen, hydroxy, halo especially chloro or bromo, $C_{1-3}$-alkyl or $C_{1-3}$-alkoxy.

A subgeneric group of compounds of this invention are those of formula I in which:

$R^1$ and $R^2$ are n-propyl-n-propyl, n-propyl-n-butyl or n-propyl-4′-hydroxyphenethyl;

$R^3$ is hydrogen; and $R^4$ is 4-hydrogen or 4-hydroxy.

In each of the above groups of compounds, the 1,3-benzthiazol-2(3H)-ones are preferred.

The pharmaceutically acceptable, acid addition salts having the utility of the free bases of formula I are also part of this invention. These are prepared by methods well known to the art and are formed with both inorganic or organic acids, for example: maleic, fumaric, benzoic, ascorbic, pamoic, succinic, bismethylenesalicylic, methane sulfonic, ethane disulfonic, acetic, oxalic, propionic, tartaric, salicylic, citric, gluconic, aspartic, stearic, palmitic, itaconic, glycolic, glutamic, benzenesulfonic, hydrochloric, hydrobromic, sulfuric, cyclohexylsulfamic, phosphoric and nitric acids. The hydrohalic and, especially, methane sulfonic acid salts are conveniently used.

Included in this invention are the O—$C_{2-6}$-alkanoyl derivatives of the compounds of formula I when a hydroxyl group is present in the structure. These are prepared by O-acylation of tertiary amine compounds of formula I, preferably using the salt form, with a lower alkanoyl halide or anhydride.

The compounds of formula I are prepared by the following reaction:

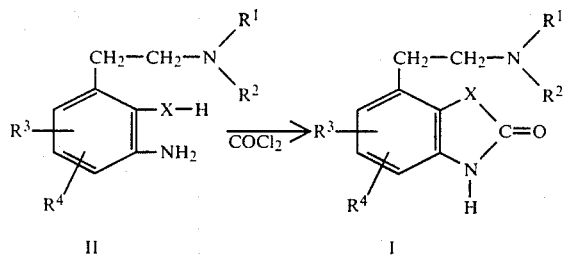

in which $R^{1-4}$ and X are as defined above except that any reactive chemical centers should be in protected form such as ether derivatives at hydroxy groups or a Boc or Cbz derivative at primary or secondary amino groups.

The reaction is carried out by reacting the o-aminophenol or o-aminothiophenol (II) with an excess of phosgene in an inert organic solvent such as benzene, toluene, methylene chloride, ethyl acetate, ether, dimethylformamide or tetrahydrofuran. The reactants are present with the phosgene in excess. The reaction proceeds rapidly to completion at from room temperature to the reflux temperature of the reaction material. The product is, then, isolated and purified by standard chemical methods.

Any protective groups are, optionally, removed by standard ether or amide splitting reactions which do not affect the hetero ring of the nucleus. For example, excess boron tribromide in methylene chloride at from −50° to room temperature has been found to give satisfactory yields for O-dealkylation. The ether derivatives, especially the methyl ethers at $R^3$ and $R^4$, have dopaminergic activity at higher dosage quantities than do their hydroxy parents.

Also, if desired, the reactive halo substituents at $R^3$ and $R^4$ are removed by standard dehalogenation reactions, especially using stoichiometric quantities, or more, of sodium-lower alcohol at reflux temperature until the reaction is complete. Once again, as the data presented below demonstrate, the compounds of formula I whose structures have halo substituents in the benz ring are less active than are their des-halo congeners but the former still have substantial dopaminergic activity.

If one, or both, of $R^1$ and $R^2$ in the compounds of formula I is hydrogen, these compounds may be further N-alkylated by methods known to the art such as reductive alkylation followed by removal of any protective groups as noted above. Direct N-alkylation can also be used to insert $R^1$ and $R^2$ substituents, such as using allyl or benzyl chloride in the presence of base. Reaction conditions for catalytic hydrogenation, however, must be used sparingly for the benzthiazolone series.

The o-aminophenols and o-aminothiophenols of formula II above as well as their acid addition salts suitable for synthetic use are important intermediates whose successful preparation is critical in the reaction sequence to prepare the end products of formula I. The preparation of the phenols (II) is accomplished either by inserting the —XH moiety when the amino group is already present or by inserting the amine when the —XH moiety is already present. In the case of the benzoxazol-2(3H)-one series, the amine is conveniently prepared via carboxy→acyl halide→acyl azide→amino transformations at the position ortho to the hydroxy group. In the case of the benzthiazol-2(3H)-one series, the aniline is reacted with sulfur monochloride or bromide to form a S-halobenzdithiazole which is reacted in situ with a reducing agent such as sodium or potassium hydrosulfite to form the desired o-aminothiophenol (II, X=S). Details of the preparation of the o-aminophenol and o-aminothiophenol starting materials (II) are presented in the illustrative examples below.

The compounds of formula I which have one or both of $R^3$ and $R^4$ as halo, i.e. chloro or bromo, either by design for blocking purposes or by a side reaction, are reacted under chemical reducing conditions such as using sodium or potassium-lower alkanol to remove the halo groups to give the relatively more active des-halo compounds.

The compounds of this invention have utility, as potent dopamine agonists, in the treatment of disorders of the cardiovascular system, especially to treat hypertension, to treat angina pectoris, to treat the symptoms of congestive heart failure or to improve kidney function by increasing renal blood flow.

More specifically, the compounds of this invention are peripheral $D_2$-agonists. Otherwise speaking, the main focus of action is at the presynaptic dopaminergic receptors whicy may also be called "$D_2$-receptors." Activation of the $D_2$-receptors on the sympathetic nerve terminals inhibits the release of norepinephrine, thereby, promoting vasodilation, among other beneficial cardiovascular actions, and decreasing sympathetic side-effects caused by norepinephrine release in certain abnormal cardiovascular conditions.

Exemplary of the $D_2$-agonist activity of the compounds of this invention are results obtained in the standard perfused rabbit ear artery protocol [J. P. Hieble et al., Arch. Pharmacol. 309 217 (1979)] as follows:

A. 4-hydroxy-7-[2-(di-n-propylamino)ethyl]-1,3-benzthiazol-2(3H)-one (hydrobromide); $EC_{50}$, 0.2 nM.
B. 4-hydroxy-6-chloro-7-[2-(di-n-propylamino)ethyl]-1,3-benzthiazol-2(3H)-one (hydrobromide); 50 nM.
C. 4-hydroxy-7-[2-(di-n-propylamino)ethyl]-1,3-benzoxazol-2(3H)-one (hydrobromide); 8 nM.
D. dopamine; 40 nM.
E. 8-hydroxy-5-[2-(di-n-propylamino)ethyl]-carbostyril; 200 nM.
F. 7-hydroxy-4-[2-(di-n-propylamino)ethyl]-2(3H)-indolone (hydrobromide); 2nM.

These data demonstrate the potent nature of the $D_2$-agonist activity of the compounds of this invention as well as the particular advantage of the 1,3-benzthiazol-2(3H)-one series. Compound A is some 40 times more potent in this protocol than its oxa congener and 10 times more potent than the corresponding indolone. Generally speaking, the generic group of compounds of this invention demonstrate $D_2$-agonism in the rabbit ear artery protocol at an $EC_{50}$ range of from 0.2 to 100 nM.

The pharmaceutical compositions of this invention which have pharmacodynamic activity within the cardiovascular system, for example renal vasodilatation, correcting hemodynamic imbalance, anti-anginal activity, antihypertensive activity and bradycardia, are prepared in conventional dosage unit forms. These incorporate a compound of formula I, or a pharmaceutically acceptable, acid addition salt or ester thereof, into a nontoxic pharmaceutical carrier according to accepted pharmacy procedures. A nontoxic unit quantity sufficient to produce the desired pharmacodynamic activity in a subject, animal or human, is used. Preferably, the compositions will contain the chemical compound in an active but nontoxic quantity selected from the range of about 10 mg to about 300 mg, preferably about 25–150 mg, calculated as the base, per dosage unit. This quantity depends on the relative potency of the chosen base compound, its specific biological activity desired, its route of administration, that is, whether oral or parenteral, and the condition and size of the patient.

The pharmaceutical carrier employed for the dosage units is, for example, either a solid or liquid. Exemplary of solid carriers are lactose, terra alba, sucrose, talc, gelatin, agar, pectin, acacia, magnesium stearate or stearic acid. Exemplary of liquid carriers are isotonic saline for parenteral use or syrup, peanut oil, olive oil or water for soft gelatin capsules. Similarly, the carrier or diluent may include any time delay material well known to the art, such as cellulose esters or ethers and glyceryl esters alone or admixed with a wax. Such sustained release products as well as prodrug derivatives which may be gradually metabolized to the active parent in vivo can be employed to prolong the unique biological activity of the compounds of this invention or to attack receptors at a specific location.

A wide variety of pharmaceutical forms can be employed. Thus, if a solid carrier for oral or rectal administration is used, the mixed preparation can be tableted, placed in a hard gelatin capsule in powder or sustained release pellet form, in a suppository or in the form of a troche or lozenge. The amount of solid carrier will vary widely but, preferably, will be from about 25 mg to about 1 g. If a liquid carrier is used, the preparation will be in the form of a syrup, emulsion, soft gelatin capsule, sterile injectable liquid such as an ampul or drip bottle as well as an aqueous or nonaqueous liquid suspension for oral administration.

Advantageously, doses selected from the dosage unit ranges given above will be administered several times, such as from one to five times, a day. The daily dosage regimen is preferably selected from the range of about 10 mg to about 750 mg, preferably 25–500 mg, for oral administration and 10–250 mg for parenteral administration. When the method described above is carried out, $D_2$-agonist activity is produced with the manifestations on abnormal cardiovascular conditions outlined above.

For an average size human and using 4-hydroxy-7-[2-(di-n-propylamino)ethyl]-1,3-benzthiazol-2(3H)-one hydrobromide as an active ingredient, a typical dose to show anti-hypertensive activity would be a $D_2$-agonist, nontoxic quantity which is selected from the range of from about 10–150 mg of base for each dosage unit, which is adapted for oral administration and which is administered orally from 1–4 times daily.

The following examples are designed solely to illustrate the preparation and use of the compounds of this invention. The temperatures are Centigrade. Other variations of these examples will be obvious to those skilled in the art.

EXAMPLE 1

4-Hydroxyphenylacetic acid (50 g, 0.32 m) in 300 ml of glacial acetic acid was cooled to 10° at which temperature 100 ml of nitric acid was slowly added. The mixture was allowed to reach room temperature, then was poured into 1 l of water. The separated solid was washed with water and recrystallized from ethanol to give 35 g of 4-hydroxy-3-nitrophenylacetic acid, m.p. 144°–146°.

A mixture of the nitro compound and 100 ml of thionyl chloride was heated at reflux for 3.5 hours, then stripped with toluene twice to leave a yellow solid acid chloride. This was dissolved in chloroform and added dropwise to 109 ml of di-n-propylamine in 200 ml of methylene chloride. The solution was washed with 10% hydrochloric acid and water. The dried solution was stripped. The residue was recrystallized from aqueous methanol, then cyclohexane to give 30 g of N,N-n-propyl-3-nitro-4-hydroxyphenylacetamide, m.p. 63°–65°.

The amide (28 g, 0.1 m) was mixed with 80 ml of water/dimethylformamide, then 36 g (0.26 m) of potassium carbonate. The red mixture was maintained at 35° while 15 ml (0.16 m) of methyl sulfate was added dropwise with stirring. The reaction mixture was quenched in 250 ml of water and extracted with ethyl acetate. The extract was washed with alkali, water, acid and brine. After drying and stripping the extract, the methyl ether remained.

A mixture of 14.7 g (0.05 m) of this methoxy compound and 100 ml of tetrahydrofuran was stirred while 100 ml (0.1 m) of 1.0 M boron hydride in tetrahydrofuran was added. The mixture was heated at reflux for 2 hours. 10% Hydrochloric acid (100 ml) was added and refluxing continued for 1 hour. The mixture was stripped, then 100 ml of 10% hydrochloric acid added. The product was extracted into methylene chloride which was dried and stripped. The residue was placed under low reduced pressure suction for 2 hours to give 16 g of a yellow oil; N,N-di-n-propyl-3-nitro-4-methoxyphenethylamine hydrochloride.

The tertiary amine (16 g, 0.05 m) was taken up in 250 ml of ethanol and hydrogenated with 0.1 g of platinum oxide at low pressure for 9 hours. The filtered reaction mixture was stripped to give 12.7 g of crude N,N-di-n-propyl-3-amino-4-methoxyphenethylamine hydrochloride. After recrystallization from isopropanol/ether 7.5 g of white solid, m.p. 139°–141°, was recovered.

A mixture of 2.86 g (0.01 m) of the phenethylamine hydrochloride, 8.2 g (0.061 m) of sulfur monochloride and 10 ml of glacial acetic acid was stirred at room temperature for 1 hour, in an oil bath at 80°–95° and, finally, at reflux for 3 hours. The mixture was diluted with 100 ml of toluene. The supernatent liquid was decanted, then the residue was taken up in water. After adjusting the pH to 5 with sodium bicarbonate, the mixture is treated with excess sodium hydrosulfite. The aqueous mixture was extracted with chloroform. The extract was dried, filtered and stripped to leave a crude product which was partially purified over a silica column using methanol/chloroform eluant. The major product weighed 1.4 g. It was recrystallized from isopropanol/ether to give 0.91 g of a yellow solid, m.p. 193°–5° (dec.), mass spectrum weight 316; 2-amino-3-methoxy-5-chloro-6-[2-(di-n-propylamino)-ethyl]-thiophenol. An aliquot (100 mg) of this compound in ether is reacted with hydrogen chloride gas to separate the salt.

A mixture of 0.64 g (0.002 m) of the thiophenol and 15 ml of toluene was stirred vigorously while 8.0 g (0.01 m) of phosgene was added. After stirring and heating at reflux for 3 hours, the residue from the filtered reaction mixture was washed with toluene and petroleum ether to give 0.71 g (93%) of a tan solid, 4-methoxy-6-chloro-7-[2-(di-n-propylamino)ethyl]-1,3-benzthiazol-2(3H)-one hydrochloride; infrared spectrum absorption at 1700 cm$^{-1}$

This reaction was repeated on a larger scale (14.3 g of amine) to give 5.98 g of o-aminothiophenol and 5.6 g of benzthiazolone.

EXAMPLE 2

The hydrochloride product from Example 1 (0.4 g) was dissolved in 10 ml of methylene chloride and cooled to −50°. Boron tribromide (0.75 ml) was added in complete solution and the mixture allowed to come to room temperature. After 4 hours, the solvent is evaporated. After adding 15 ml of methanol, the mixture was chilled to −78° and stripped. The residue was treated with several portions of cold methanol and stripping, then was recrystallized from methanol to give 0.17 g (39%) of 4-hydroxy-6-chloro-7-[2-(di-n-propylamino)ethyl]-1,3-benzthiazol-2(3H)-one hydrobromide, m.p. 284°–6° (dec.).

Anal. Calcd. for $C_{15}H_{21}ClN_2O_2S\cdot HBr$: C, 43.96; H, 5.41; N, 6.84: Found: C, 43.68; H, 5.31; N, 6.64.

EXAMPLE 3

A 5 g sample of the hydrochloride salt of the product of Example 1 was treated with 5% aqueous sodium bicarbonate and the mixture extracted with chloroform. The extract was dried and evaporated to give 4.1 g of the free base.

The base (4.1 g) is taken into 80 ml of xylene and 13 ml of amyl alcohol. The mixture was added dropwise to a mixture of 2.75 g of sodium and 50 ml of xylene while refluxing. Additional sodium (0.75 g) was added. The product residue was purified over a silica column using an ethyl acetate-methanol eluant system. The product containing fractions were dried and evaporated to give 0.6 g of an oil which crystallized under hexane to give 4-methoxy-7-[2-di-n-propylamino)ethyl]-1,3-benzthiazol-1(3H)-one as the base.

Later fractions proved to elute the des-chloro-o-aminothiophenol (0.66 g) as an oily base. This material was reacted with phosgene (8.0 g) in toluene to give 0.81 g of 4-methoxy-7-[2-di-n-propylamino)ethyl]-1,3-benzthiazol-1(3H)-one as the hydrochloride salt.

EXAMPLE 4

The hydrochloride of the 4-methoxybenzthiazolone product from Example 3 (0.58 g), in 30 ml of methylene chloride, was reacted with 0.80 ml of boron tribromide at room temperature overnight. The mixture was cooled to −78° to add 15 ml of cooled methanol. The mixture was stripped and the residue treated with methanol several times. The inactivated residue mixture was taken into boiling ethanol/methanol. The volume of the solution was reduced to 20 ml on a steam bath. Cooling separated 0.47 g of a tan solid; 4-hydroxy-7-[2-(di-n- propylamino)ethyl]-1,3-benzthiazol-2(3H)-one hydrobromide, m.p. 259°–61°.

Anal. Calcd. for $C_{15}H_{22}N_2O_2S \cdot HBr$: C, 48.00; H, 6.18; N, 7.46. Found: C, 47.95; H, 6.08; N, 7.37.

A sample (50 mg) was converted to the base as described above. Part of the base was reacted with an excess of methane sulfonic acid in methylene chloride to give the methane sulfonate salt.

EXAMPLE 5

A mixture of 100 g of 2,4-dimethoxybenzaldehyde, 102 ml of nitromethane, 46.4 g of ammonium acetate and 500 ml of glacial acetic acid was heated at reflux for 2 hours and quenched in 700 ml of water. The crude precipitate was recrystallized from ethanol to give 105.57 g of 1-(2,4-dimethoxyphenyl)-2-nitroethylene as a yellow solid.

The ethylene compound in 500 ml of tetrahydrofuran was added to 36.7 g of lithium aluminum hydride in 500 ml of ether. After a reflux period of 1.5 hours, the mixture was combined with 184 ml of 1N sodium hydroxide solution. The resulting cake was separated by filtration and washed with 200 ml of hot tetrahydrofuran. The ethereal extracts and mother liquors were stripped. The residual oil was taken into chloroform, dried and stripped to give 94.9 g of 2,4-dimethoxyphenethylamine as an oil.

A mixture of 94.9 g (0.524 m) of the phenethylamine and 102 g (0.786 m) of propionic anhydride was heated on the steam bath for 45 minutes, then treated with 300 ml of 10% sodium hydroxide solution. The pH was adjusted to 6 and, then, 8. The mixture was extracted with chloroform. The dried extract was evaporated. The oily residue was extracted with boiling cyclohexane. The extracted material was recrystallized from ether-petroleum ether (4:1) to give the white solid N-propionyl derivative; 49.2 g (39%), m.p. 71°–3°.

This material in 200 ml of tetrahydrofuran was mixed with 415 ml of borane. After refluxing the mixture for 1 hour, it was acidified with 400 ml of 10% hydrochloric acid. The mixture was heated at reflux for 1.5 hours. The ethereal solvent was evaporated in vacuo. The alkali washed and dried extract was evaporated to give N-n-propyl-2,4-dimethoxyphenethylamine.

The reductive alkylation procedure was repeated to give 47.7 g of N,N-di-n-propyl-2,4-dimethoxyphenethylamine.

A mixture of 45 g (0.17 m) of the tertiary amine and 450 ml of ether was stirred in a water bath while 225 ml of butyl lithium was added slowly. The stirred reaction mixture was saturated with dry carbon dioxide. The mixture was shaken with 4×200 ml of water. The aqueous extract was taken to pH 6 with concentrated hydrochloric acid, then extracted with ether (3×200 ml). After the aqueous mixture was taken to pH 1, it was extracted with chloroform (4×200 ml). The extract was dried and stripped to leave a solid which was purified using acetonitrile-ether to give 23.25 g (40%) of 3-[2-(di-n-propylamino)ethyl]-2,6-dimethoxybenzoic acid, m.p. 174°–177°.

A mixture of 23.25 g (0.0673 m) of the benzoic acid and 100 ml of thionyl chloride was stirred and, then, heated at reflux for 2 hours. After stripping and toluene azeotroping the residue, the residual acid chloride was stored overnight in the cold. It was, then, dissolved in 150 ml of dry acetone and stirred in an ice bath while 8.99 g (0.138 m) of sodium azide in 45 ml of water was added. After 1 hour, the mixture was diluted with 400 ml of water, then extracted well with chloroform. The dried extracts were stripped at 30° in vacuo. The residue was dissolved in methylene chloride and added slowly to boiling toluene.

The mixture was heated at reflux for 1 hour and, then, the solvent removed under vacuum. To the residue was added 50 ml of 10% hydrochloric acid. The mixture was heated on a steam bath for 1 hour. The cooled mixture was taken to pH 12 and extracted with chloroform. After drying and pumping under high vacuum, the extracted material was 13.48 g (71%) of 3-[2-(di-n-propylamino)ethyl]-2,6-dimethoxyaniline.

A mixture of 1.94 g (0.00693 m) of the aniline, 0.86 g (0.0138 m) of ethyl mercaptan, 0.66 g (0.0138 m) of sodium hydride and 20 ml of dimethylformamide was stirred at room temperature briefly, then heated at reflux for 1 hour. The cooled mixture was poured into 30 ml of water. The pH was adjusted to 3 and the quench was extracted with pentane It was then readjusted to pH 7, salted and extracted with chloroform (5×25 ml). The dried extract was stripped and vacuum pumped at 50°–70°. The residue was purified over a silica column using a chloroform-methanol eluant system. The product containing fractions (TLC) were stripped and pumped to give 0.87 g (47%) of a brown oil which is 2-amino-3-methoxy-6-[2-(di-n-propylamino)ethyl]-phenol.

A mixure of 2.15 g (0.0081 m) of the o-aminophenol, 9.58 g (0.0116 m) of phosgene and 40 ml of toluene was heated at reflux for 1 hour. Excess phosgene was boiled off and the residue stripped. The residue was purified over 60 g of silica using chloroform/methanol eluant to give 0.71 g (30%) of 4-methoxy-7-[2-(di-n-propylaminoethyl]-1,3-benzoxazol-2(3H)-one hydrochloride.

EXAMPLE 6

A solution of the methoxy hydrochloride (1.2 g, 0.00525 m) in 60 ml of methylene chloride was cooled to −30° at which time 14.64 ml of a 1 M solution of boron tribromide in methylene chloride was added. After stirring at room temperature overnight, the reaction mixture was stripped. The residue was treated with methanol (5×30 ml) with evaporation. The residue was recrystallized from ethanol/ether to give 0.98 g (52%) of 4-hydroxy-7-[2-(di-npropylamino)ethyl]-1,3-benzoxazol-2(3H)-one hydrobromide, m.p. 220°–222°.

Anal. Calcd. for $C_{15}H_{22}N_2O_3 \cdot HBr$: C, 50.14; H, 6.17; H, 7.79. Found: C, 50.01; H, 6.42; N, 7.65.

EXAMPLE 7

Substituting N-n-propyl-N-n-butyl-3-amino-4-methoxyphenethylamine for the di-n-propyl diamine in Examples 1–4 gives 4-methoxy-6-chloro-7-[2-(n-propyl-n-butylamino)ethyl]-1,3-benzthiazol-2(3H)-one hydrochloride and, also, 4-hydroxy-7-[2-(n-propyl-n-butylamino)ethyl]-1,3-benzthiazol-2(3H)-one hydrobromide.

Substituting N,N-di-n-propyl-3-amino-4,6-dichlorophenethylamine in Examples 1 and 3 gives 4,6-dichloro-7-[2-(di-n-propylamino)ethyl]-1,3-benzthiazol-2(3H)-one hydrochloride and 7-[2-(di-n-propylamino)ethyl]-1,3-benzthiazol-2(3H)-one base and hydrochloride salt.

Substituting N,N-di-n-propyl-3-amino-4-methylphenethylamine in Examples 1 and 3 above gives 4-methyl-6-chloro-7-[2-(di-n-propylamino)ethyl]-1,3-benzthiazol-2(3H)-one hydrochloride and 4-methyl-7-

[2-(di-n-propylamino)ethyl]-1,3-benzthiazol-2(3H)-one hydrobromide.

Substituting N-n-propyl-N-4-methoxyphenethyl-3-amino-4-methoxyphenethylamine in Examples 1, 3 and 4 gives the 4-methoxy and the 4-hydroxy-7-[2-(n-propyl-4-hydroxyphenethylamino)ethyl]-1,3-benzthiazol-2(3H)-one hydrobromides.

Using the general reaction sequences outlined in detail above and amino protecting groups such as benzyloxycarbonyl (Cbz) or trifluoroacetyl (TFA) groups gives:

7-(2-aminoethyl)-1,3-benzthiazol-2(3H)-one base and its methylsulfonate salt;

4-hydroxy-7-[2-(n-propylamino)ethyl]-1,3-benzthiazol-2(3H)-one base and its hydrochloride salt;

4-hydroxy-7-[2-(n-propylamino)ethyl]-1,3-benzoxazol-2(3H)-one base and its hydrochloride salt;

4-hydroxy-7-[2-(methylamino)ethyl]-1,3-benzoxazole-2(3H)-one base or its ethanedisulfonate salt.

EXAMPLE 8

4-Hydroxy-7-[2-(di-n-propylamino)-ethyl]-1,3-benzthiazol-2(3H)-one hydrobromide (25 mg of base) is mixed with 200 mg of lactose and 2 mg of magnesium stearate, filled into a hard gelatin capsule and administered orally to a hypertensive human patient from 1-4 times daily.

What is claimed is:

1. A chemical compound of the formula:

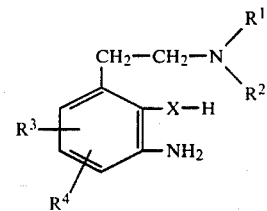

in which:
X is —S— or —O—;
$R^1$ and $R^2$ are, each, $C_{1-6}$-alkyl, allyl, benzyl, phenethyl or methoxyphenethyl; and
$R^3$ and $R^4$ are, each, hydrogen, halo, $C_{1-3}$-alkyl or $C_{1-3}$-alkoxy, or an acid addition salt thereof.

2. The compound of claim 1 being 2-amino-3-methoxy-5-chloro-6-[2-(di-n-propylamino)ethyl]-thiophenol.

3. The compound of claim 1 being 2-amino-3-methoxy-6-[2-(di-n-propylamino)ethyl]-thiophenol.

4. The compound of claim 1 being 2-amino-3-methoxy-6-[2-(di-n-propylamino)ethyl]-phenol.

* * * * *